United States Patent
Pettit et al.

(10) Patent No.: US 6,620,911 B1
(45) Date of Patent: Sep. 16, 2003

(54) ANTI-CRYPTOCOCCAL PEPTIDES

(75) Inventors: George R. Pettit, Paradise Valley, AZ (US); Robin K. Pettit, Fountain Hills, AZ (US)

(73) Assignee: Arizona Board of Regents, acting for and on behalf of Arizona State University, Tempe, AZ (US)

( * ) Notice: Subject to any disclaimer, the term of this patent is extended or adjusted under 35 U.S.C. 154(b) by 0 days.

(21) Appl. No.: 09/582,951

(22) PCT Filed: Jan. 8, 1999

(86) PCT No.: PCT/US99/00418
§ 371 (c)(1),
(2), (4) Date: Jul. 7, 2000

(87) PCT Pub. No.: WO99/35164
PCT Pub. Date: Jul. 15, 1999

Related U.S. Application Data (60) Provisional application No. 60/070,879, filed on Jan. 9, 1998, and provisional application No. 60/091,705, filed on Jul. 3, 1998.

(51) Int. Cl.[7] .................................................. C07K 5/10
(52) U.S. Cl. ........................ 530/330; 530/331; 514/18; 514/19
(58) Field of Search ............................... 530/330, 331; 514/18–19

(56) References Cited

U.S. PATENT DOCUMENTS 5,504,191 A * 4/1996 Pettit .......................... 530/330

* cited by examiner

*Primary Examiner*—Christopher S. F. Low
*Assistant Examiner*—David Lukton
(74) *Attorney, Agent, or Firm*—Richard R. Mybeck; Susan Stone Rosenfield

(57) ABSTRACT

Antifungals based on dolasatin 10 and four structural modifications thereof (herein "peptides") and methods of treating a host afflicted with a fungi-induced infection are herein described. In broth macrodilution assays, these peptides were fungicidal for ATCC stains and clinical isolates of *Cryptococcus neoformans*. Specificity for *C. neoformans* was also demonstrated in the solid-phase disk diffusion assay, and fungicidal activity confirmed in killing kinetics experiments. Broth macrodilution minimum inhibitory and minimum fungicidal concentrations for the most potent modification ranged from 0.0975–1.56 μg/ml and 0.0975–6.24 μg/ml respectively. The minimum inhibitory concentrations were nearly identical in the presence of human serum, but increased with lowered pH. Suitable dosage forms for use of the novel antifungals are also described.

18 Claims, 3 Drawing Sheets

FIG. 1a

Dolastatin 10
(Dov-Val-Dil-Dap-Doe)

FIG. 1b

Dov-Val-Dil-Dap-Phe-3-[(5-phenyl)-1,4-thiadiazolamide]

FIG. 1c

Dov-Val-Dil-Dap-Phe-3-[(5-thiomethyl)-1,4-thiadiazolamide]

FIG. 1d

Dov-Val-Dil-Dap-Phe-OMe

FIG. 1e

Dov-Val-Dil-Dap-Met-3-quinolylamide

FIG. 2

ANTI-CRYPTOCOCCAL PEPTIDES

This application claims the benefit of provisional applications 60/070,879 filed Jan. 9, 1998 and 60/091,705 filed Jul. 3, 1998.

This research was funded in part by Outstanding Investigator Grant CA44344-01-09 awarded by the National Cancer Institute, DHHS. The United States government may have certain rights to this invention.

The present invention relates generally to the treatment of one or more fungal diseases and more particularly, to the discovery that selected structural modifications of dolastatin 10 are remarkably useful as fungicides.

The elucidation and isolation of dolastatin 10 is described in U.S. Pat. No. 4,816,444 which issued to G. R. Pettit et al., on Mar. 28, 1989 while early efforts to synthesize dolastatin 10 and develop certain modifications thereof are described in U.S. Pat. Nos. 4,978,744; 5,410,024; 5,504,191; 5,521,284; 5,530,097; 5,599,902; 5,635,483; 5,663,149; and 5,665,860, all of which issued to G. R. Pettit et al. between 1990 and 1997. The general background information from each of the above cited U.S. patents is incorporated herein by this reference thereto.

Dolastatin 10 is a linear peptide containing four unusual amino acids (compound 1a, FIG. 1) and was originally isolated from the Indian Ocean sea hare *Dolabella auricularia* (See: Pettit et al., The isolation and structure of a remarkable marine animal antineoplastic constituent: Dolastatin 10, *J Am Chem Soc* 1987, 109: 6883–85). The synthesis of dolastatin 10 (Pettit et al., The absolute configuration and synthesis of natural (-)-dolastatin 10, *J Am Chem 1 Soc* 1989, 111: 5463–65; Pettit et al., Dolastatins 24. Synthesis of (-)-dolastatin 10. X-ray molecular structure of N,N-dimethylvalyl-valyl-dolaisoleuinetert-butyl ester, *J Chem Soc, Perkin Trans* 1 1996, 859–63) facilitated detailed investigation of its powerful antineoplastic activities (see, Pettit, The dolastatins., In: Herz et al., (eds.) *Progress in the Chemistry of Organic Natural Products,* 70th edn. New York: Springer-Verlag, 1997: 1–79), culminating in the initiation of Phase I cancer clinical trials in 1995. The sea hare-derived peptide dolastatin 10 is currently in phase I and phase II cancer clinical trials. In mammalian cells, the intracellular target of dolastatin 10 is tubulin. The peptide inhibits microtubule assembly and tubulin-dependent GTP binding (Bai et al., Dolastatin 10, a powerful cytostatic peptide derived from a marine animal: Inhibition of tubulin polymerization mediated through the vinca alkaloid binding domain, *Biochem Pharmacol* 1990, 39 (12): 1941–49), and is a noncompetitive inhibitor of vincristine binding to tubulin (Bai et al., Binding of dolastatin 10 to tubulin at a distinct site for peptide antimitotic agents near the exchangeable nucleotide and vinca alkaloid sites, *J Biol Chem* 1990, 265 (28): 17141–49). Dolastatin 10 causes metaphase arrest in a wide variety of animal and human cancer cell lines, and exhibits impressive activity in murine tumor models (see Pettit, 1997, supra). In addition, dolastatin 10 induces apoptosis in certain human lymphoma cells lines (Beckwith et al., Growth inhibition of human lymphoma cell lines by the marine products, dolastatins 10 and 15, *J Nat Cancer Inst* 1993, 85 (6): 483–88; Maki et al., The bcl-2 and p53 oncoproteins can be modulated by bryostatin 1 and dolastatins in human diffuse large cell lymphoma, *Anti-Cancer Drugs* 1995, 6: 392–97). The apoptotic mechanism is apparently unrelated to its antimitotic effects (Beckwith et al., 1993, supra; Maki et al., 1995, supra). In ongoing clinical trials in patients with advanced solid tumors, there is minimal toxicity at doses up to 200 $\mu g/m^2$ (Tran et al., A Phase I, pharmacokinetic/pharmacodynamic study of dolastatin 10 in adult patients with advanced solid tumors, Proceedings of the American Association for Cancer Research, San Diego, Calif. 1997, #2056; Bagniewski et al., Pharmacokinetics of dolastatin 10 in adult patients with solid tumors, Proceedings of the American Association for Cancer Research, San Diego, Calif. 1997, #1492; McElroy et al., Phase I trial of dolastatin 10 in patients with advanced solid tumors, Proceedings of the American Society of Clinical Oncology, Denver, Colo. 1997, #782).

The tubulin-binding properties discovered for dolastatin 10 prompted a further look to consider whether dolastatin 10 might also be useful as an antifungal agent. The effort resulted in dolastatin 10 and four specific structural modifications thereof (FIG. 1) being identified as potent and specific fungicidals which are specifically active against *Cryptococcus neoformans*.

The antifungal spectrum of dolastatin 10 and four structural modifications thereof has been evaluated and is disclosed herein. In broth macrodilution assays, the peptides were fungicidal for ATCC strains and clinical isolates (including fluconazole-resistant strains) of *Cryptococcus neoformans*, but not for any of the other yeasts or filamentous fungi examined. Specificity for *C. neoformans* was also demonstrated in the solid-phase disk diffusion assay, and fungicidal activity was confirmed in killing kinetics experiments. The MICs at which 50% and 90% of 19 clinical isolates were inhibited ($MIC_{50}$, $MIC_{90}$) by a methyl ester modification were 0.195 $\mu g/ml$ and 0.39 $\mu g/ml$, respectively. The $MFC_{50}$, (minimum fungicidal concentration) for this peptide was 0.39 $\mu g/ml$, and the $MFC_{90}$ was 0.78 $\mu g/ml$. Broth macrodilution minimum inhibitory and minimum fungicidal concentrations for the most potent modification ranged from 0.0975–1.56 $\mu g/ml$ and 0.0975–6.24 $\mu g/ml$, respectively. The minimum inhibitory concentrations (MICs) were nearly identical in the presence of human serum, but increased with lowered pH. These peptides offer untoward promise as potential chemotherapeutics for *C. neoformans*, a leading cause of infection and mortality in immunocompromised patients.

Accordingly, the prime object of the present invention is to provide new anti-cryptococcal peptides and methods of using same.

Another object of the present invention is to provide the elucidation and identification of dolastatin 10 and structural modifications thereof for use as fungicides.

These and still further objects as shall hereinafter appear are readily fulfilled by the present invention in a remarkably unexpected manner as will be readily discerned fiom the following detailed description of exemplary embodiments thereof especially when read in conjunction with the drawings attached hereto.

DETAILED DESCRIPTION OF THE INVENTION

Materials and Methods

Antifungal Agents

Dolastatin 10 1a and modification 1d (FIG. 1) were synthesized as described elsewhere (Pettit et al., 1989, supra; Pettit et al., 1996, supra, Pettit et al., Antineoplastic agents 365. Dolastatin 10 SAR probes, *Anti-Cancer Drug Design* 1997: In press). Synthesis of modification 1e is described in U.S. Pat. No. 5,663,149 (issued Sep. 2, 1997), and synthesis of modifications 1b and 1c are described in pending U.S. applications Ser. No. 60/070,879 and No. 60/091,705. The compounds were reconstituted in sterile dimethylsulfoxide (DMSO) immediately prior to all assays. DMSO alone had no detectable inhibitory effect on any of the tested microbes.

Fungal Strains

Clinical isolates of *C. neoformans* were obtained from patient cerebrospinal fluid, blood, bone marrow, sputum, bronchial lavage and wound infections at the University of Virginia Medical Center, Strains clinically resistant to fluconazole (See: Jessup, C. J. et al, 1997; Poster #F-88, 37th ICAAC, Toronto, Canada) were provided by the Center for Medical Mycology, Case Western Reserve University. Yeast strains (except for *C. albidus* and *C. laurentii*) were maintained by single colony transfer on Sabouraud Dextrose Agar (SDA), pH 5.6 at 35° C. *Cryptococcus albidus, C. laurentii* and *C. uniguttulatus* (#66033) were maintained on SDA, pH 6.6 at 25° C., *C. uniguttulatus* (#34143) and *C. ater* on Yeast Morphology (YM) agar at 25° C. and filamentous fungi were maintained on Potato Dextrose Agar (PDA) slants at 35° C.

Disk Diffusion Susceptibility Testing

Antimicrobial activity was assayed by disk susceptibility tests according to the NCCLS (National Committee for Clinical Laboratory Standards, Performance Standards for Antimicrobial Disk Susceptibility Tests-Sixth Edition: Approved standard M2-A6, NCCLS, Wayne, Pa., 1997). Inocula were adjusted to a density of 0.10 at 625 nm in SDA broth, and spread on SDA plates. Excess moisture was allowed to absorb for 10 min before applying dried disks containing two-fold dilutions of the drugs. Test plates were incubated at 35° C. (25° C. for *C. albidus* and *C. laurentii*), and zones of inhibition recorded after 48 h. The minimum inhibitory concentration (MIC) was defined as the lowest concentration of drug resulting in a clear zone of growth inhibition. Disk susceptibility testing of *Staphylococcus aureus, Enterococcus faecalis, Escherichia coli* and *Neisseria gonorrhoeae* was also performed.

Broth Macrodilution Susceptibility Testing of Yeasts

Dolastatin 10 and modifications were screened against yeasts by the broth macrodilution assay according to the NCCLS (National Committee for Clinical Laboratory Standards, Reference Method for Broth Dilution Antifungal Susceptibility Testing of Yeasts: Approved Standard M27-A, NCCLS, Wayne, Pa., 1997). Yeasts were suspended and diluted as recommended to yield final inocula ranging from $0.5-2.5\times10^3$ colony forming units (CFU)/ml. Tests were performed in sterile 12×75 mm plastic tubes containing two-fold dilutions of the peptides in 0.165 M morpholinepropanesulfonic acid (MOPS)-buffered RPMI 1640 medium (pH 7.0). One tube was left drug-free for a turbidity control. Tubes were incubated without agitation at 35° C. (25° C. for *C. albidus* and *C. laurentii*). MICs were determined after 72 h for Cryptococcus, and after 48 h for other yeast genera. The MIC was defined as the lowest concentration of compound that inhibited all visible growth of the test organism.

Broth Macrodilution Susceptibility Testing of Filamentous Fungi

Broth macrodilution susceptibility testing of *Aspergillus fumigatus* and *Rhizopus oligosporus* was performed according to a proposed standardized procedure (Espinel-Ingroff et al., Multicenter evaluation of a proposed standardized procedure for antifungal susceptibility testing of filamentous fungi, *J Clin Microbiol* 1997, 35: 139–43) with slight modification. To induce conidium and sporangiospore formation, *A. fumigatus* and *R. oligosporus* were grown on PDA slants at 35° C. for 6 days. Fungal slants were covered with 1 ml of sterile 0.85% NaCl, and suspensions made by gently probing the colonies with the tip of a sterile pasteur pipette. The resulting mixture of hyphal fragments and conidia or sporangiospores was withdrawn, transferred to a sterile clear microfuge tube, and heavy particles were allowed to settle for 10 min. The upper homogeneous suspension was then transferred to a sterile microfuge tube, vortexed at 15 s, adjusted spectrophotometrically, and diluted in sterile 0.165M MOPS-buffered RPMI 1640 medium, pH 7.0, to yield final inocula ranging from $0.5-2.5\times10^3$ CFU/ml. Susceptibility to the synthetic peptides was then determined by broth macrodilution assays as described above for the yeast cultures. MICs for the filamentous fungi were read after 24 h.

Minimum Fungicidal Concentrations

Minimum fungicidal concentrations (MFCs) were determined by subculturing 0.1 ml from each tube with no visible growth in the MIC broth macrodilution series onto drug-free SDA plates. The plates were incubated at 35° C. for 48 h for Cryptococcus (25° C. for *C. alhidus* and *C. laurentii*), and 35° C. for 24 h for all other yeast and filamentous fungi. The MFC was defined as the lowest concentration of drug that completely inhibited growth on SDA plates.

Effect of Host Factors

Broth macrodilution assays were performed with RPMI prepared at pH 5, pH 6 and pH 7, and in RPMI, with and without 50% normal human serum (Lampire Biological Labs). *Cryptococcus neoformans* #90112 was used in each case.

Killing Kinetics

Overnight cultures of *C. neoformans* (#90112) in Ph 7.0 MOPS-buffered RPMI 1640 medium were inoculated into the same medium containing multiples of the broth macrodilution MIC of the antifungal peptides, or an equivalent volume of DMSO. Cultures were shaken at 35° C., and aliquots aseptically removed at various times for dilution plating.

Results and Discussion

The initial screen for antimicrobial activity, the disk diffusion assay, suggested that dolastatin 10 and four analogs had narrow-spectrum antifungal activity (Table 1). Futhermore, at 100 µg/disk there was no inhibition of the tested bacterial strains (see, Materials and Methods, supra). The specificity for *C. neoformans* was confirmed by broth macrodilution (Table 2). As with the disk diffusion technique, the parent compound was not growth inhibitory to the related species *C. albidus* and *C. laurentii. C. uniguttulatus* and *C. ater*. The MFCs for *C. neoformans* were typically identical or twofold greater than MICs. Exceptions occurred with *C. neoformans* #14116, where MFCs with compounds 1b and 1c were sixteenfold greater than MICs. Dolastatin 10 was also fuigicidal for strains of *C. neoformans* that were clinically resistant to fluconazole (Jessup et al., supra) (Table 3). As the methyl ester 1d was the most potent antifungal peptide in broth macrodilution tests, it was tested against 19 clinical isolates (did not include fluconazole-resistant stains) of *C. neoformans*. No resistant clinical isolates were found.

TABLE 1

Antifungal activity of dolastatin 10 (1a) and modifications (1b-1e) in the disk diffusion assay.

| Organism | ATCC# | MIC μg/disk | MIC μg/disk | MIC μg/disk |
|---|---|---|---|---|
| | | 1a | 1b | 1c |
| Cryptococcus neoformans | 90112 | 25–50 | 3.12–6.25 | 1.56–3.12 |
| Cryptococcus albidus | 66030 | >100 | >100 | |
| Cryptococcus laurentii | 66036 | >100 | >100 | |
| Candida albicans | 90028 | >100 | >100 | >100 |
| Candida glabrata | 90030 | >100 | >100 | >100 |
| | | 1d | 1e | |
| Cryptococcus neoformans | 90112 | 3.12–6.25 | 25–50 | |
| Cryptococcus albidus | 66030 | >100 | | |
| Cryptococcus laurentii | 66036 | >100 | | |
| Candida albicans | 90028 | >100 | >100 | |
| Candida glabrata | 90030 | | | |

TABLE 2

Antifungal activity of dolastatin 10 (1a) and modifications (1b–1e) in the broth macrodilution assay.

| Organism | ATCC# | MIC μg/ml | MFC μg/ml | MIC μg/ml | MFC μg/ml | MIC μg/ml | MFC μg/ml |
|---|---|---|---|---|---|---|---|
| | | 1a | | 1b | | 1c | |
| Cryptococcus neoformans | 66031 | 0.78 | 1.56 | 0.78 | 0.78 | 0.78 | 0.78 |
| Cryptococcus neoformans | 14116 | 3.12 | 6.25 | 1.56 | 25 | 0.78 | 12.5 |
| Cryptococcus neoformans | 32045 | 0.78 | 1.56 | 0.78 | 0.78 | 0.78 | 1.56 |
| Cryptococcus neoformans | 90112 | 0.78 | 1.56 | 1.56 | 3.12 | 0.78 | 0.78 |
| Cryptococcus albidus | 66030 | >50 | | | | | |
| Cryptococcus albidus[a] | 34140 | >50 | | | | | |
| Cryptococcus albidus | 10666 | >50 | | | | | |
| Cryptococcus laurentii | 66036 | >50 | | | | | |
| Cryptococcus laurentii | 18803 | >50 | | | | | |
| Cryptococcus laurentii[a] | 34142 | >50 | | | | | |
| Cryptococcus uniguttulatus[a] | 34143 | >50 | | | | | |
| Cryptococcus uniguttulatus | 66033 | >50 | | | | | |
| Cryptococcus ater[a] | 14247 | >50 | | | | | |
| Candida albicans | 90028 | >50 | | >25 | >25 | | |
| Candida glabrata | 90030 | >50 | | >50 | >50 | | |
| Candida parapsilosis | 22019 | >50 | | | | | |
| Candida lusitaniae | 42720 | >50 | | | | | |
| Rhodotorula mucilaginosa | 9449 | >50 | | | | | |
| Aspergillus fumigatus | 96918 | >50 | | | | | |
| Rhizopus oligosporus | 22959 | >50 | | | | | |
| | | 1d | | 1e | | | |
| Cryptococcus neoformans | 66031 | 0.195 | 0.39 | 0.78 | 1.56 | | |
| Cryptococcus neoformans | 14116 | 1.56 | 3.12 | 12.5 | >50 | | |

TABLE 2-continued

Antifungal activity of dolastatin 10 (1a) and modifications (1b–1e) in the broth macrodilution assay.

| Organism | ATCC# | MIC μg/ml | MFC μg/ml | MIC μg/ml | MFC μg/ml | MIC μg/ml | MFC μg/ml |
|---|---|---|---|---|---|---|---|
| Cryptococcus neoformans | 32045 | 0.195 | 0.39 | 0.78 | 0.78 | | |
| Cryptococcus neoformans | 90112 | 0.0975 | 0.195 | 1.56 | 6.25 | | |
| Cryptococcus albidus | 66030 | | | | | | |
| Cryptococcus albidus[a] | 34140 | | | | | | |
| Cryptococcus albidus | 10666 | | | | | | |
| Cryptococcus laurentii | 66036 | | | | | | |
| Cryptococcus laurentii | 18803 | | | | | | |
| Cryptococcus laurentii[a] | 34142 | | | | | | |
| Cryptococcus uniguttulatus[a] | 34143 | | | | | | |
| Cryptococcus uniguttulatus | 66033 | | | | | | |
| Cryptococcus ater[a] | 14247 | | | | | | |
| Candida albicans | 90028 | >50 | | >50 | | | |
| Candida glabrata | 90030 | >50 | | >50 | | | |
| Candida parapsilosis | 22019 | | | | | | |
| Candida lusitaniae | 42720 | | | | | | |
| Rhodotorula mucilaginosa | 9449 | | | | | | |
| Aspergillus fumigatus | 96918 | | | | | | |
| Rhizopus oligosporus | 22959 | | | | | | |

For 19 clinical isolates of *C. neoformans*, the MICs at which 50% and 90% of the isolates were inhibited ($MIC_{50}$, $MIC_{90}$) by modification 1d were 0.195 μg/ml and 0.39 μg/ml, respectively. The $MFC_{50}$ for modification 1d was 0.39 μg/ml, and the $MFC_{90}$ was 0.78 μg/ml. The clinical isolate MICs for analog 1d ranged from 0.0975–0.78 μg/ml, and MFCs ranged from 0.0975–6.24 μg/ml. For more than 68% of the clinical isolates, MFC/MIC ratios were less than or equal to 2, and for 26% of the isolates, the ratio equaled 4. The MFCs obtained after the recommended incubation period and one week later were compared. There was no evidence of recovery.

Figure 1A:
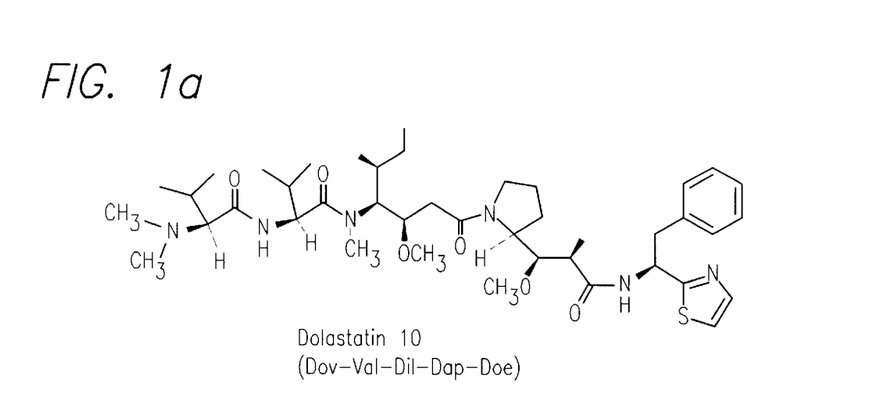
FIG. 1 shows the chemical sires of dolastatin 10 (1*a*) and derivatives (1*b*–1*e*).
Figure 1B:
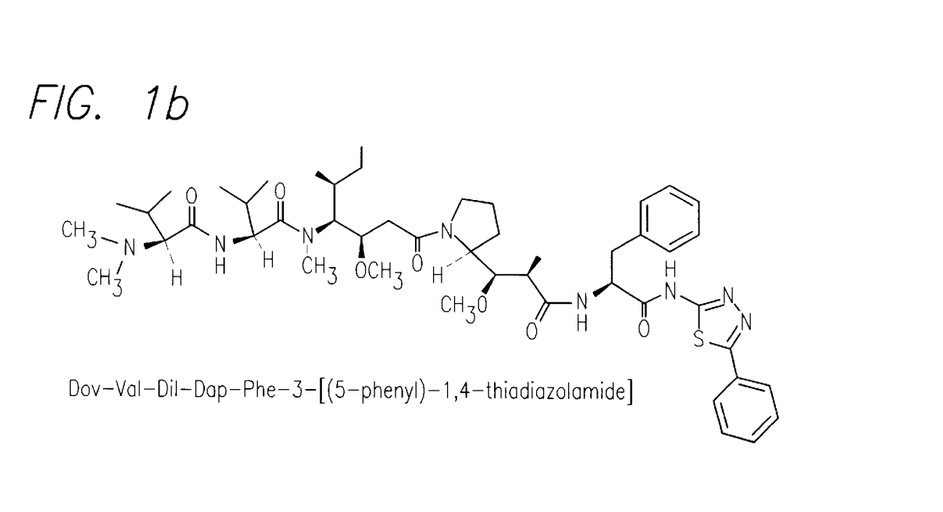
Figure 1C:
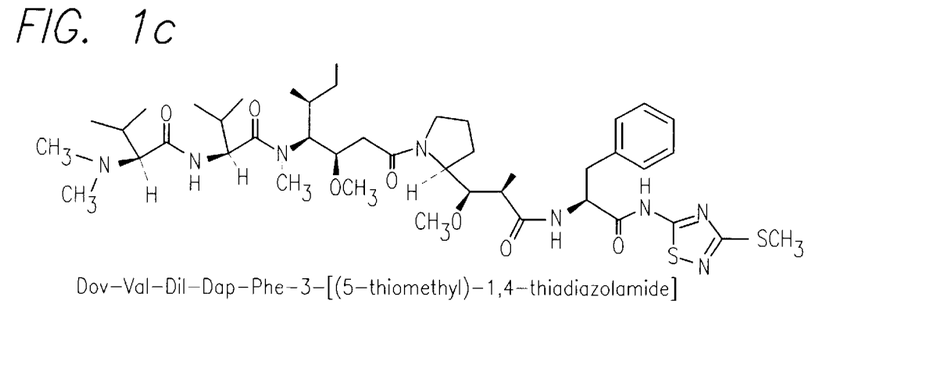
Figure 1D:
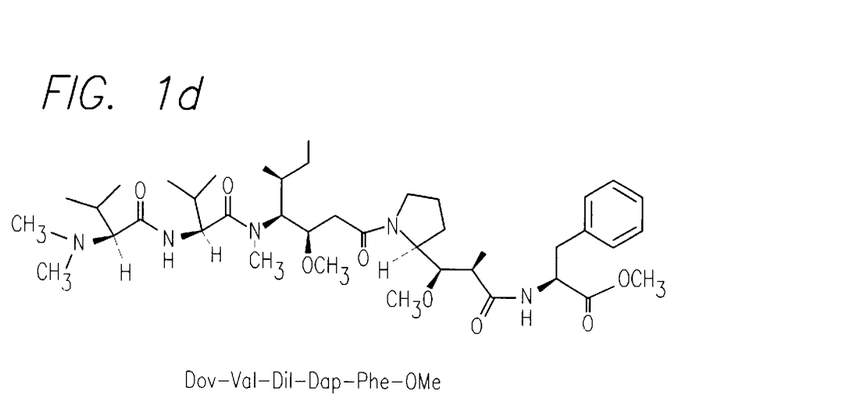
Figure 1E:
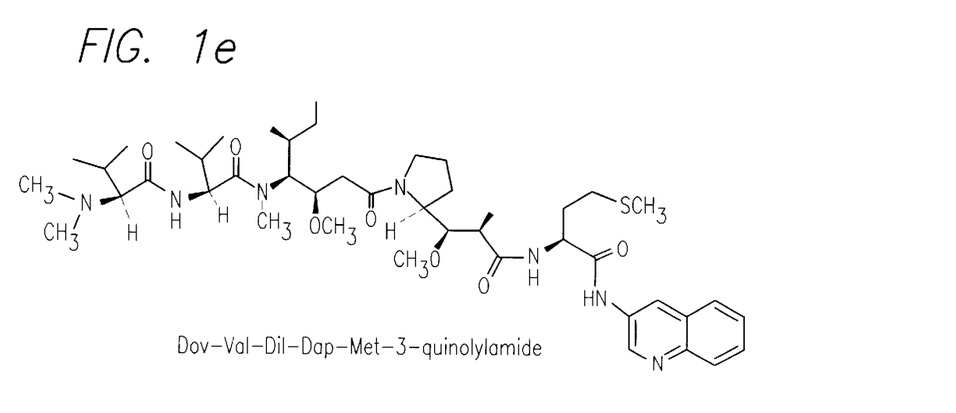
Figure 2:
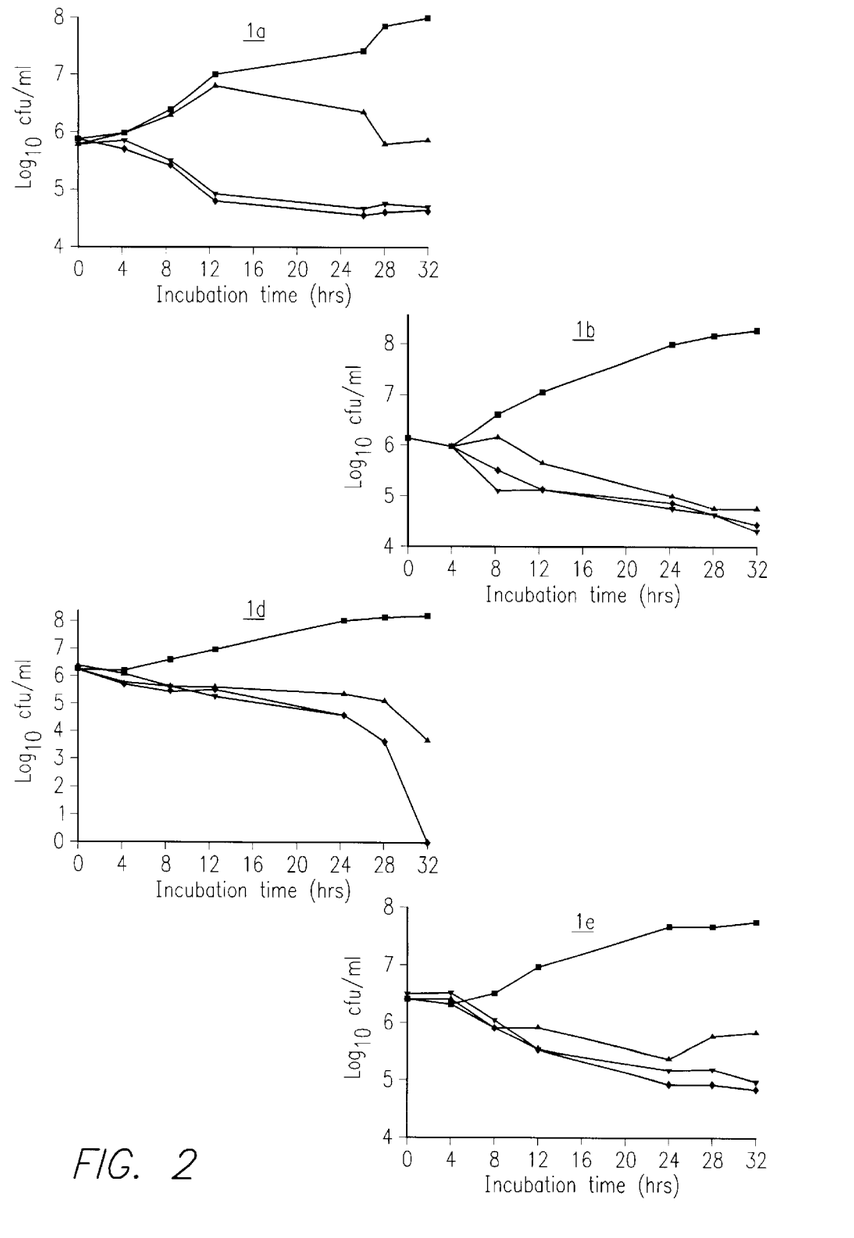
FIG. 2 shows the *Cryptococcus neoformans* killing kinetics of dolastatin 10 and selected modifications where "killing" is shown as squares (no drug), triangles (1×MIC), inverted triangles (4×MIC), and diamonds (8×MIC) for each compound.

The fungicidal action of four of the peptides was confirmed in killing kinetics experiments (FIG. 2) (a paucity of modification 1c prohibited killing kinetics). In general, killing was concentration dependent between 1x and 4x the MIC, but not between 4x and 8x the MIC. The most dramatic reductions in CFUs were obtained with modification 1d.

Dolastatin 10 and three of the modifications were available in sufficient quantity to investigate the effects of two host factors, pH and serum, on broth macrodilution MICs and MFCs. The MICs and MFCs increased in acidified RPMI (Table 4). The anticryptococcal activity of modification 1d was the least affected by lowered pH. Attempts were made to obtain MICs at pH 8, but the strain did not grow in alkaline RPMI.

TABLE 3

Inhibidon of fluconazole-resistant[a] *Cryptococcus neoformans* by dolastatin 10(1a)

| Strain | MIC (μg/ml) | MFC (μg/ml) |
|---|---|---|
| 94-2406 | 0.0487 | 0.0975 |
| 95-2792 | 0.78 | 3.12 |
| 94-2011 | 0.78 | 1.56 |
| 94-2483 | 0.195 | 0.39 |

[a]Jessup, supra

TABLE 4

Effect of pH on MICs and MFCs of dolastatin 10 (1a) and modifications (1b, 1d, 1e) for *Cryptococcus neoformans*.

| | 1a | | 1b | | 1d | | 1e | |
|---|---|---|---|---|---|---|---|---|
| pH | MIC μg/ml | MFC μg/ml | MIC μg/ml | MFC μg/ml | MIC μg/ml | MFC μg/ml | MIC μg/ml | MFC μg/ml |
| 5 | >50 | >50 | 50 | >50 | 1.56 | 3.12 | >50 | >50 |
| 6 | 6.25 | 25 | 1.56 | 3.12 | 0.39 | 0.78 | 6.25 | 25 |
| 7 | 0.78 | 1.56 | 0.39 | 0.78 | 0.0975 | 0.195 | 0.78 | 1.56 |

To ascertain whether the increased concentration of dolastatin 10 required to kill *C. neoformans* in acidified media was due to loss of peptide activity, or more rapid growth of the test organism, two controls were performed. Dolastatin 10 was incubated at pH 5, pH 6 and pH 7 under the same conditions as the broth macrodilution assay, and $GI_{50}s$ (concentration required to inhibit 50% of cell growth) for six human cancer cell lines (pancreas BXPC-3, neuroblastoma SK-N-SH, thyroid SW1736, non-small cell lung NCI-H460, pharynx FADU, prostate DU-145) compared. Acid treated dolastatin 10 had no apparent loss of antiproliferative activity (data not shown). In the second control, optical densities over time were compared in shake flasks containing *C. neoformans* in pH 5, pH 6 or pH 7 RPMI media. Growth rates at pH 5 and pH 6 were identical, and the growth rate at pH 7 only slightly slower (data not shown). The increased MICs and MFCs of dolastatin 10 in acidified media cannot be explained. Possible explanations include more rapid uptake of the peptides at neutral pH owing to increased permeability or activation of transport mechanisms, or that the ionization state of dolastatin 10 affects interaction with its fungal target (the human cancer cell line control suggests that the ionization state of dolastatin 10 does not affect interaction with its mammalian tubulin target). Certainly, the increased MICs at lowered pH do not eliminate the potential of these compounds for clinical antifungal development. Widely prescribed antimicrobials with increased MICs in acidic media include streptomycin, erythromycin, gentamicin, and metronidazole (for a review see, Amsterdam, Susceptibility testing of antimicrobials in liquid media, Lorian (ed.) *Antibiotics in laboratory medicine*, Maryland: Williams & Wilkins, 1996: 52–111).

In vitro, dolastatin 10 is stable in human, dog and mouse plasma for at least 24 h at 37° C. (Newman et al., Preclinical pharmacology of the natural marine product dolastatin 10 (NSC 376128), *Drug Metabolism and Disposition* 1994, 22 (3): 428–32). After intravenous injection into mice, the estimated elimination half-life is 5.6 h (Newman et al., 1994, supra). In the presence and absence of human serum, MICs and MFCs of the peptides for *C. neoformans* were very similar (Table 5). For compounds 1d and 1e, MICs and MFCs were actually lower in the presence of human serum. Activity of the peptides in serum from two different suppliers (Sigma, Lampire) was similar (data not shown).

TABLE 5

Effect of human serum on MICs and MFCs of dolastatin 10 (1a) and modifications (1b, 1d, 1e) for *Cryptococcus neoformans*.

| | 1a | | 1b | | 1d | | 1e | |
|---|---|---|---|---|---|---|---|---|
| Treatment | MIC μg/ml | MFC μg/ml | MIC μg/ml | MFC μg/ml | MIC μg/ml | MFC μg/ml | MIC μg/ml | MFC μg/ml |
| no serum | 0.78 | 1.56 | 1.56 | 1.56 | 0.195 | 0.39 | 1.56 | 3.12 |
| 50% human serum | 0.78 | 1.56 | 1.56 | 3.12 | 0.0975 | 0.0975 | 0.78 | 0.78 |

From the foregoing, a related series of novel anticryptococcal agents were defined. In human cancer clinical trials, the parent compound appears to have minimal toxicity at doses up to 455 $\mu g/m^2$ (Tran et al., 1997, supra; Bagniewski et al., 1997, supra; McElroy et al., 1997, supra). The incidence of invasive fungal infection in cancer patients ranges from approximately 5% to 30% (Meunier, Current clinical issues on mycoses in neutropenic patients, *Int J Antimucrobal Agents* 1996, 6: 135–40), and *C. neoformans* is a leading cause of such infection (Samonis et al., Fungal infections in cancer patients: An escalating problem, In vivo, 1992, 6: 183–94). Given the encouraging clinical toxicity data, it is apparent that the peptides herein described constitute a valuable addition to the limited arsenal of treatments currently available for patients inflicted with cryptococcoses. By the criteria evaluated herein, modification 1d appears to be the most promising candidate for future in vivo cryptococcal protection studies. Given their specificity for *C. neoformans*, these peptides should also be examined as a potential means to rapidly identify *C. neoformans* in clinical settings.

The dosage administered will be dependent upon the identity of the fungus; the location of the fungal infection; the type of host involved; the nature of concurrent treatment, if any; and the frequency of treatment specified.

Illustratively, dosage levels of the administered active ingredients are: intravenous, 0.1 to about 6 μg/kg; orally, 0.1 to about 30 μg/kg; intramuscular, 0.1 to about 6 μg/kg; intranasal instillation, 0.1 to about 30 μg/kg; and aerosol, 0.1 to about 30 μg/kg of host body weight.

Expressed in terms of concentration, an active ingredient can be present in the compositions of the present invention for localized use about the cutis, intranasally, pharyngolaryngeally, bronchially, intravaginally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in salves and ointments for topical application although unit dosage forms, such as tablets, capsules, pills, powders, granules, suppositories, sterile parenteral solutions or suspensions, sterile non-parenteral solutions or suspensions, lozenges and the like, containing suitable quantities of an active ingredient will also provide effective delivery of the active ingredient under selected circumstances.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavoring oil.

Capsules are produced by preparing a powder mixture as hereinbefore described and filling into formed gelatin sheaths. Advantageously, as an adjuvant to the filling operation, a lubricant such as talc, magnesium stearate, calcium stearate and the like is added to the powder mixture before the filling operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously, the tablet can be provided with a protective coating consisting of a sealing coat or enteric coat of shellac, a coating of sugar and methylcellulose and polish coating of carnauba wax.

Fluid unit dosage forms for oral administration such as in syrups, elixirs and suspensions can be prepared wherein each teaspoonful of composition contains a predetermined amount of an active ingredient for administration. The water-soluble forms can be dissolved in an aqueous vehicle together with sugar, flavoring agents and preservatives to form a syrup. An elixir is prepared by using a hydroalcoholic vehicle with suitable sweeteners together with a flavoring agent. Suspensions can be prepared of the insoluble forms with a suitable vehicle with the aid of a suspending agent such as acacia, tragacanth, methylcellulose and the like.

For parenteral administration, fluid unit dosage forms are prepared utilizing an active ingredient and a sterile vehicle, water being preferred. The active ingredient, depending on the form and concentration used, can be either suspended or dissolved in the vehicle. In preparing solutions the active ingredient can be dissolved in a suitable vehicle for injection and filter sterilized before filling into a suitable vial or ampule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the vaginal route may be utilized when warranted. An active ingredient can also be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, a fluid instillation, a fluid unit dosage form is prepared utilizing an active ingredient and a suitable pharmaceutical vehicle, preferably pyrogen free ("P.F.") water. A dry powder can be formulated when insufflation is the administration of choice.

For use as aerosols, the active ingredients can be packaged in a pressurized aerosol container together with a gaseous or liquified propellant, for example, dichlorodifluoromethane, carbon dioxide, nitrogen, propane, and the like, with the usual adjuvants such as cosolvents and wetting agents, as may be necessary or desirable.

In a preferred practice for the treatment of dermatological fungi, the active ingredient will be delivered to the site as an ointment or salve which will comprise water and oil emulsion as the principal carrier. Other conventional ingredients, when conditions and aesthetics dictate, include petrolatum and mineral oil, lipophilic solubilizers such as polyethylene glycol, carbowax, moisturizers such as lanolin and fragrance.

The term "unit dosage form" as used in the specification and claims refers to physically discrete units suitable as unitary dosages for human and animal subjects, each unit containing a predetermined quantity of active material calculated to produce the desired therapeutic effect in association with the required pharmaceutical diluent, carrier or vehicle. The specifications for the novel unit dosage forms of this invention are dictated by and are directly dependent on (a) the unique characteristics of the active material and the particular therapeutic effect to be achieved, and (b) the limitation inherent in the art of compounding such an active material for therapeutic use in humans, as disclosed in this specification, these being features of the present invention. Examples of suitable unit dosage forms in accord with this invention are tablets, capsules, troches, suppositories, powder packets, wafers, cachets, teaspoonfuls, tablespoonfuls, dropperfuls, ampules, vials, segregated multiples of any of the foregoing, and other forms as herein described.

The active ingredients to be employed as antifungal agents can be easily prepared in such unit dosage form with the employment of pharmaceutical materials which themselves are available in the art and can be prepared by established procedures. The following preparations are illustrative of the preparation of the unit dosage forms of the present invention, and not as a limitation thereof. Several dosage forms were prepared embodying the present invention. They are shown in the following examples in which the notation "active ingredient" signifies one of the compounds designated as dolastatin 10 or the modifications thereof as set forth herein.

Composition "A"

Hard-Gelatin Capsules

One thousand two-piece hard gelatin capsules for oral use, each capsule containing 2 mg of an active ingredient are prepared from the following types and amounts of ingredients:

| | |
|---|---|
| Active ingredient, micronized | 2 gm |
| Corn Starch | 20 g |
| Talc | 20 g |
| Magnesium stearate | 2 g |

The active ingredient, finely divided by means of an air micronizer, is added to the other finely powdered ingredients, mixed thoroughly and then encapsulated in the usual manner.

The foregoing capsules are useful for treating a fungal disease by the oral administration of one or two capsules one to four times a day.

Using the procedure above, capsules are similarly prepared containing an active ingredient in 0.1, 5, and 20 mg amounts by substituting 0.1 gm, 5 gm and 20 gm of an active ingredient for the 2 gm used above.

Composition "B"

Soft Gelatin Capsules

One-piece soft gelatin capsules for oral use, each containing 2 mg of an active ingredient, finely divided by means of an air micronizer, are prepared by first suspending the compound in 0.5 ml of corn oil to render the material capsulatable and then encapsulating in the above manner.

The foregoing capsules are useful for treating a fungal disease by the oral administration of one or two capsules one to four times a day.

Composition "C"

Tablets

One thousand tablets, each containing 2 mg of an active ingredient, are prepared from the following types and amounts of ingredients:

| | |
|---|---|
| Active ingredient, micronized | 10 gm |
| Lactose | 300 gm |
| Corn Starch | 50 g |
| Magnesium stearate | 4 g |
| Light liquid petrolatum | 5 gm |

The active ingredient, finely divided by means of an air micronizer, is added to the other ingredients and then thoroughly mixed and slugged. The slugs are broken down by forcing them through a Number Sixteen screen. The resulting granules are then compressed into tablets, each tablet containing 2 mg of the active ingredient.

The foregoing tablets are useful for treating a fungal disease by the oral administration of one or two tablets one to four times a day.

Using the procedure above, tablets are similarly prepared containing an active ingredient in 0.1 mg, 5 mg and 20 mg amounts by substituting 0.1 gm, 5 gm and 20 gm of an active ingredient for the 2 gm used above.

Composition "D"

Oral Suspension

One liter of an aqueous suspension for oral use, containing in each teaspoonful (5 ml) dose, 2 mg of an active ingredient, is prepared from the following types and amounts of ingredients:

| | |
|---|---|
| Active ingredient, micronized | 0.4 grams |
| Citric acid | 2 gm |
| Benzoic acid | 1 gm |
| Sucrose | 790 gm |
| Tragacanth | 5 gm |
| Lemon Oil | 2 gm |
| Deionized water, q.s. 1000 ml | |

The citric acid, benzoic acid, sucrose, tragacanth and lemon oil are dispersed in sufficient water to make 850 ml of suspension. The active ingredient, finely divided by means of an air micronizer, is stirred into the syrup unit uniformly distributed. Sufficient water is added to make 1000 ml.

The composition so prepared is useful for treating a fungal disease at a dose of 1 teaspoonful (15 ml) three times a day.

Composition "E"

Parenteral Product

One liter of a sterile aqueous suspension for parenteral injection, containing 400 µg of an active ingredient in each milliliter for treating a fungal disease, is prepared from the following types and amounts of ingredients:

| | |
|---|---|
| Active ingredient, micronized | 400 mg |
| POLYSORBATE 80 | 5 gm |
| Methylparaben | 2.5 gm |
| Propylparaben | 0.17 gm |
| Water for injection, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is filled into sterile vials and the vials sealed.

The composition so prepared is useful for treating a fungal disease at a dose of 1 milliliter (1 ml) one to three times a day.

Composition "F"

Suppository, Rectal and Vaginal

One thousand suppositories, each weighing 2.5 gm and containing 2 mg of an active ingredient are prepared from the following types and amounts of ingredients:

| | |
|---|---|
| Active ingredient, micronized | 0.15 gm |
| Propylene glycol | 150 gm |
| Polyethylene glycol #4000, q.s. | 2,500 gm |

The active ingredient is finely divided by means of an air micronizer and added to the propylene glycol and the mixture passed through a colloid mill until uniformly dispersed. The polyethylene glycol is melted and the propylene glycol dispersion is added slowly with stirring. The suspension is poured into unchilled molds at 40° C. The composition is allowed to cool and solidify and then removed from the mold and each suppository foil wrapped.

The foregoing suppositories are inserted rectally or vaginally for treating a fungal disease when appropriate.

Composition "G"

Intranasal Suspension

One liter of a sterile aqueous suspension for intranasal instillation, containing 2 mg of an active ingredient in each milliliter, is prepared from the following types and amounts of ingredients:

| | |
|---|---|
| Active ingredient, micronized | 2 gm |
| POLYSORBATE 80 | 5 gm |
| Methylparaben | 2.5 gm |
| Propylparaben | 0.17 gm |
| Deionized water, q.s. 1000 ml. | |

All the ingredients, except the active ingredient, are dissolved in the water and the solution sterilized by filtration. To the sterile solution is added the sterilized active ingredient, finely divided by means of an air micronizer, and the final suspension is aseptically filled into sterile containers.

The composition so prepared is useful for treating a fungal disease, by intranasal instillation of 0.2 to 1.0 ml given one to four times per day.

An active ingredient can also be present in the undiluted pure form for use locally about the cutis, intranasally, pharyngolaryngeally, bronchially, or orally.

Composition "H"

Powder

Five grams of an active ingredient in bulk form is finely divided by means of an air micronizer. The micronized powder is placed in a shaker-type container.

The foregoing composition is useful for treating a fungal disease, at localized sites by applying a powder one to four times per day.

Composition "I"

Oral Powder

Ten grams of an active ingredient in bulk form is finely divided by means of an air micronizer. The micronized powder is divided into individual doses of 2 mg and packaged.

The foregoing powders are useful for treating a fungal disease, by the oral administration of one or two powders suspended in a glass of water, one to four times per day.

Composition "J"

Insufflation

Ten grams of an active ingredient in bulk form is finely divided by means of an air micronizer.

The foregoing composition is useful for treating a fungal disease, by the inhalation of 2 mg one to four times a day.

Composition "K"

Ointment

One hundred grams of an active ingredient in bulk form is finely divided by means of an air micronizer. The micronized powder is then admixed into a water and oil emulsion with the addition of suitable moisturizers and fragrances as desired.

The foregoing ointment is useful for treating a fungal disease by topical application of the ointment on the affected area as needed, preferably at least twice a day.

From the foregoing, it becomes readily apparent that a new and useful antifungal agent and new and useful antifungal preparations have been herein described and illustrated which fulfill the aforestated object in a remarkably unexpected fashion. It is, of course, understood that such modifications, alterations and adaptations as will readily occur to the artisan confronted with this disclosure are intended within the spirit of the present invention which is limited only by the scope of the claims appended hereto.

What is claimed is:

1. A method of inhibiting growth of a fungus in a host that is infected with a fungus comprising administering to said host a composition comprising an acceptable carrier, and a compound selected from the group consisting of formulae 1a, 1b, 1c, 1d, and 1e, wherein said method, said composition is administered to the host for a time and under conditions effective to inhibit growth of said fungus; and wherein the structures of said formulae are as follows:

1a, Dolastatin 10
(Dov-Val-Dil-Dap-Doe)

1b, Dov-Val-Dil-Dap-Phe-3[(5-phenyl)-1,4-thiadiazolamide]

-continued

1c, Dov-Val-Dil-Dap-Phe-3-[(5-thiomethyl)-1,4-thiadiazolamide]

1d, Dov-Val-Dil-Dap-Phe-OMe

1e, Dov-Val-Dil-Dap-Met-3-quinolylamide

2. The method according to claim 1 wherein said fungus is *Cryptococcus neoformans*.

3. The method according to claim 2 wherein said host is a mammal.

4. The method according to claim 3 in which said mammal is a human.

5. The method according to claim 3 in which said composition is administered to said human by parenteral means.

6. The method according to claim 3 in which said composition is administered topically to said human.

7. The method according to claim 4 in which said composition is administered intravenously to said human.

8. The method according to claim 4 in which said active ingredient is administered in a suppository inserted in said host.

9. The method according to claim 3 in which said composition is administered to said mammal by parenteral means.

10. The method according to claim 3 in which said composition is administered topically to said mammal.

11. The method according to claim 3 in which said composition is administered intravenously to said mammal.

12. The method according to claim 3 in which said composition is administered in a suppository inserted in said mammal.

13. The method according to claim 3 wherein said mammal is infected systematically with *Cryptococcus neoformans*.

14. The method according to claim 3 wherein the epidermis of said mammal is infected with *Cryptococcus neoformans*.

15. The method according to claim 10 wherein said carrier is selected from the group consisting of a water-and-oil emulsion, petrolatum, mineral oil, a moisturizer, and a solubilizer.

16. The method according to claim 6 wherein said carrier is selected from the group consisting of a water-and-oil emulsion, petrolatum, mineral oil, a moisturizer, and a solubilizer.

17. The method of claim 10 in which said carrier contains a fragrance.

18. The method of claim 16 in which said carrier contains a fragrance.

* * * * *

UNITED STATES PATENT AND TRADEMARK OFFICE
CERTIFICATE OF CORRECTION

PATENT NO.        : 6,620,911 B1  
APPLICATION NO. : 09/582951  
DATED             : September 16, 2003  
INVENTOR(S)       : Pettit et al.

Page 1 of 1

It is certified that error appears in the above-identified patent and that said Letters Patent is hereby corrected as shown below:

- Column 16, line 7, in claim 5, the text "claim 3" should be changed to -- claim 4 --.

- Column 16, line 9, in claim 6, the text "claim 3" should be -- claim 4 --.

Signed and Sealed this

Twenty-ninth Day of September, 2009

David J. Kappos  
*Director of the United States Patent and Trademark Office*